United States Patent
Shute et al.

(10) Patent No.: US 10,993,670 B2
(45) Date of Patent: May 4, 2021

(54) DIRECT HEART SOUND MEASUREMENT USING MOBILE DEVICE ACCELEROMETERS

(71) Applicant: Cardiac Pacemakers, Inc., St. Paul, MN (US)

(72) Inventors: Jonathan B. Shute, Minnetonka, MN (US); Keith R. Maile, New Brighton, MN (US); Rezwan Ahmed, Arden Hills, MN (US); Pramodsingh H. Thakur, Woodbury, MN (US); Viktoria A. Averina, Shoreview, MN (US); Qi An, Blaine, MN (US); John D. Hatlestad, Maplewood, MN (US); Bin Mi, Plymouth, MN (US)

(73) Assignee: Cardiac Pacemakers, Inc., St Paul (MN)

( * ) Notice: Subject to any disclaimer, the term of this patent is extended or adjusted under 35 U.S.C. 154(b) by 195 days.

(21) Appl. No.: 16/132,404

(22) Filed: Sep. 15, 2018

(65) Prior Publication Data
US 2019/0083039 A1  Mar. 21, 2019

Related U.S. Application Data

(60) Provisional application No. 62/559,416, filed on Sep. 15, 2017.

(51) Int. Cl.
*A61B 5/02* (2006.01)
*A61B 5/00* (2006.01)
(Continued)

(52) U.S. Cl.
CPC .......... *A61B 5/6898* (2013.01); *A61B 5/0006* (2013.01); *A61B 5/0205* (2013.01);
(Continued)

(58) Field of Classification Search
CPC . A61B 5/6898; A61B 5/02444; A61B 5/0006; A61B 5/0205; A61B 5/7203;
(Continued)

(56) References Cited

U.S. PATENT DOCUMENTS

| | | | |
|---|---|---|---|
| 6,650,940 B1 * | 11/2003 | Zhu | A61N 1/36542 600/528 |
| 6,978,182 B2 | 12/2005 | Mazar et al. | |

(Continued)

FOREIGN PATENT DOCUMENTS

| | | |
|---|---|---|
| CN | 203408061 U | 1/2014 |
| CN | 204698602 U | 10/2015 |

(Continued)

OTHER PUBLICATIONS

International Search Report and Written Opinion received for PCT Patent Application No. PCT/US2018/051257, dated Feb. 26, 2019, 10 pages.

*Primary Examiner* — Amanda K Hulbert
*Assistant Examiner* — Natasha Patel
(74) *Attorney, Agent, or Firm* — Faegre Drinker Biddle & Reath LLP

(57) ABSTRACT

A mobile device, having a processor, includes an accelerometer configured to generate acceleration data, the acceleration data including a plurality of acceleration measurements. The mobile device also includes a memory having embodied thereon computer-executable instructions that are configured to, when executed by the processor, cause the processor to: obtain the acceleration data from the accelerometer; and generate, based on the acceleration data, heart sound data, the heart sound data including data associated with one or more heart sounds.

20 Claims, 3 Drawing Sheets

(51) Int. Cl.
*A61B 5/024* (2006.01)
*A61B 5/0205* (2006.01)
*A61B 5/11* (2006.01)
*A61B 7/04* (2006.01)
*A61B 5/04* (2006.01)

(52) U.S. Cl.
CPC ........ *A61B 5/02444* (2013.01); *A61B 5/7203* (2013.01); *A61B 5/02438* (2013.01); *A61B 5/04017* (2013.01); *A61B 5/1102* (2013.01); *A61B 5/725* (2013.01); *A61B 7/04* (2013.01); *A61B 2562/0219* (2013.01)

(58) Field of Classification Search
CPC ..... A61B 5/1102; A61B 7/04; A61B 5/02438; A61B 5/04017; A61B 5/725; A61B 2562/0219
See application file for complete search history.

(56) References Cited

U.S. PATENT DOCUMENTS

| | | | |
|---|---|---|---|
| 2008/0004904 A1* | 1/2008 | Tran | A61B 5/4839 705/2 |
| 2011/0066041 A1* | 3/2011 | Pandia | A61B 5/029 600/484 |
| 2016/0100817 A1* | 4/2016 | Hussain | A61B 7/04 600/301 |
| 2017/0119273 A1 | 5/2017 | Thakur et al. | |
| 2017/0188862 A1 | 7/2017 | Kale et al. | |

FOREIGN PATENT DOCUMENTS

| | | |
|---|---|---|
| CN | 205083510 U | 3/2016 |
| WO | 2011/063092 A1 | 5/2011 |
| WO | 2016/149583 A1 | 9/2016 |

* cited by examiner

DIRECT HEART SOUND MEASUREMENT USING MOBILE DEVICE ACCELEROMETERS

CROSS-REFERENCE TO RELATED APPLICATION

This application claims priority to Provisional Application No. 62/559,416, filed Sep. 15, 2017, which is herein incorporated by reference in its entirety.

TECHNICAL FIELD

The present invention relates to devices and methods for monitoring one or more physiological parameters of a subject. More specifically, the invention relates to devices, systems, and methods for monitoring heart sounds using mobile device accelerometers.

BACKGROUND

The opening and closing of valves, as well as aspects of the flow of blood through the heart, produce vibrations known as heart sounds (sometimes abbreviated as "HS" herein). Heart sounds may be measured and used to indicate the heart's mechanical activities. Additionally, measurements performed with simultaneously recorded ECG and heart sounds provide for quantitative indications of the electro-mechanical association.

SUMMARY

Embodiments facilitate monitoring heart sounds using mobile devices such as, for example, smartphones, tablets, and/or the like. A heart sound analyzer instantiated by the mobile device is configured to obtain acceleration data from an accelerometer and to generate, based on the acceleration data, data associated with one or more heart sounds ("heart sound data").

In an Example 1, a mobile device having a processor, comprising: an accelerometer configured to generate acceleration data, the acceleration data comprising a plurality of acceleration measurements; a memory having embodied thereon computer-executable instructions that are configured to, when executed by the processor, cause the processor to: obtain the acceleration data from the accelerometer; and generate, based on the acceleration data, heart sound data, the heart sound data comprising data associated with one or more heart sounds.

In an Example 2, the mobile device of Example 1, further comprising a display device configured to present a representation of the heart sound data.

In an Example 3, the mobile device of either of Examples 1 or 2, wherein the computer instructions are configured to cause the processor to generate the heart sound data by: performing a data interpolation process on the acceleration data to generate standardized acceleration data; performing a noise reduction process on the standardized acceleration data; and performing a pattern recognition process on the standardized acceleration data to identify one or more heart sounds.

In an Example 4, the mobile device of Example 3, wherein performing the noise reduction process on the standardized acceleration data comprises performing at least one of: spectral filtering, bandpass filtering, and high pass filtering.

In an Example 5, the mobile device of Example 3, wherein performing the pattern recognition process comprises: identifying a heart sound window; and identifying, within the heart sound window, the one or more heart sounds.

In an Example 6, the mobile device of Example 5, wherein identifying the one or more heart sounds is performed using a template matching process.

In an Example 7, the mobile device of any of Examples 1-6, wherein the computer-executable instructions are configured to cause the processor to identify an occurrence of a trigger event and obtain the acceleration data in response to determining the occurrence of the trigger event, wherein the computer-executable instructions are configured to cause the processor to identify the occurrence of the trigger event by causing the processor to: determine that the mobile device is located at a target location on the subject; determine that the mobile device is positioned in a target position with respect to the subject; receive an indication of a user input; and/or determine that a parameter satisfies one or more trigger criteria, the parameter comprising at least a physiological parameter, an environmental parameter, and a device parameter.

In an Example 8, the mobile device of any of Examples 1-7, wherein the computer-executable instructions are further configured to cause the processor to: receive electrocardiogram (ECG) data from an ECG module; and generate the heart sound data based on the acceleration data and the ECG data.

In an Example 9, the mobile device of Example 8, wherein the computer-executable instructions are configured to cause the processor to generate the heart sound data based on the ECG data by using the ECG data to facilitate identifying one or more heart sound windows corresponding to the heart sound data.

In an Example 10, the mobile device of either of Examples 8 or 9, wherein the ECG module is: a component of the mobile device; or a component of an additional device, the additional device comprising at least one of an additional mobile device, a mobile device accessory, an implantable medical device (IMD), and an external medical device (EMD).

In an Example 11, a method of monitoring heart sounds using a mobile device having an accelerometer, the method comprising: obtaining the acceleration data from the accelerometer; and generating, based on the acceleration data, heart sound data, the heart sound data comprising data associated with one or more heart sounds.

In an Example 12, the method of Example 11, further comprising presenting, using a display device, a representation of the heart sound data.

In an Example 13, the method of either of Examples 11 or 12, wherein generating the heart sound data comprises: performing a data interpolation process on the acceleration data to generate standardized acceleration data; performing a noise reduction process on the standardized acceleration data; and performing a pattern recognition process on the standardized acceleration data to identify one or more heart sounds.

In an Example 14, a system for monitoring heart sounds, comprising: a mobile device, comprising: an accelerometer configured to generate acceleration data, the acceleration data comprising a plurality of acceleration measurements; a processor communicatively coupled to the accelerometer; and a memory having embodied thereon computer-executable instructions that are configured to, when executed by the processor, cause the processor to obtain the acceleration data from the accelerometer, and to generate, based on the acceleration data, heart sound data, the heart sound data comprising data associated with one or more heart sounds.

In an Example 15, the system of Example 14, further comprising an additional device, the additional device comprising an electrocardiogram (ECG) module configured to provide ECG data, wherein the processor is configured to receive, from the ECG module, the ECG data, and wherein the computer-executable instructions are configured to cause the processor to generate the heart sound data based on the ECG data.

In an Example 16, a mobile device having a processor, comprising: an accelerometer configured to generate acceleration data, the acceleration data comprising a plurality of acceleration measurements; a memory having embodied thereon computer-executable instructions that are configured to, when executed by the processor, cause the processor to: obtain the acceleration data from the accelerometer; and generate, based on the acceleration data, heart sound data, the heart sound data comprising data associated with one or more heart sounds.

In an Example 17, the mobile device of Example 16, further comprising a display device configured to present a representation of the heart sound data.

In an Example 18, the mobile device of Example 16, wherein the computer instructions are configured to cause the processor to generate the heart sound data by: performing a data interpolation process on the acceleration data to generate standardized acceleration data; performing a noise reduction process on the standardized acceleration data; and performing a pattern recognition process on the standardized acceleration data to identify one or more heart sounds.

In an Example 19, the mobile device of Example 18, wherein performing the noise reduction process on the standardized acceleration data comprises performing at least one of: spectral filtering, bandpass filtering, and high pass filtering.

In an Example 20, the mobile device of Example 18, wherein performing the pattern recognition process comprises: identifying a heart sound window; and identifying, within the heart sound window, the one or more heart sounds.

In an Example 21, the mobile device of Example 20, wherein identifying the one or more heart sounds is performed using a template matching process.

In an Example 22, the mobile device of Example 16, wherein the computer-executable instructions are configured to cause the processor to identify an occurrence of a trigger event, and to cause the processor to obtain the acceleration data in response to identifying the occurrence of the trigger event, wherein the computer-executable instructions are configured to cause the processor to identify the occurrence of the trigger event by causing the processor to: determine that the mobile device is located at a target location on the subject; determine that the mobile device is positioned in a target position with respect to the subject; receive an indication of a user input; and/or determine that a parameter satisfies one or more trigger criteria, the parameter comprising at least a physiological parameter, an environmental parameter, and a device parameter.

In an Example 23, the mobile device of Example 16, wherein the computer-executable instructions are further configured to cause the processor to: receive electrocardiogram (ECG) data from an ECG module; and generate the heart sound data based on the acceleration data and the ECG data.

In an Example 24, the mobile device of Example 23, wherein the computer-executable instructions are configured to cause the processor to generate the heart sound data based on the ECG data by using the ECG data to facilitate identifying one or more heart sound windows corresponding to the heart sound data.

In an Example 25, the mobile device of Example 23, wherein the ECG module is: a component of the mobile device; or a component of an additional device, the additional device comprising at least one of an additional mobile device, a mobile device accessory, an implantable medical device (IMD), and an external medical device (EMD).

In an Example 26, a method of monitoring heart sounds using a mobile device having an accelerometer, the method comprising: obtaining the acceleration data from the accelerometer; and generating, based on the acceleration data, heart sound data, the heart sound data comprising data associated with one or more heart sounds.

In an Example 27, the method of Example 26, further comprising presenting, using a display device, a representation of the heart sound data.

In an Example 28, the method of Example 26, wherein generating the heart sound data comprises: performing a data interpolation process on the acceleration data to generate standardized acceleration data; performing a noise reduction process on the standardized acceleration data; and performing a pattern recognition process on the standardized acceleration data to identify one or more heart sounds.

In an Example 29, the method of Example 26, further comprising identifying an occurrence of a trigger event, wherein the step of obtaining the acceleration data is performed in response to identifying the occurrence of the trigger event.

In an Example 30, the method of Example 26, wherein identifying the occurrence of the trigger event comprises: determining that the mobile device is located at a target location on the subject; determining that the mobile device is positioned in a target position with respect to the subject; receiving an indication of a user input; and/or determining that a parameter satisfies one or more trigger criteria, the parameter comprising at least one of a physiological parameter, an environmental parameter, and a device parameter.

In an Example 31, the method of Example 26, further comprising: receiving electrocardiogram (ECG) data; and generating the heart sound data based on the ECG data.

In an Example 32, a system for monitoring heart sounds, comprising: a mobile device, comprising: an accelerometer configured to generate acceleration data, the acceleration data comprising a plurality of acceleration measurements; a processor communicatively coupled to the accelerometer; and a memory having embodied thereon computer-executable instructions that are configured to, when executed by the processor, cause the processor to obtain the acceleration data from the accelerometer, and to generate, based on the acceleration data, heart sound data, the heart sound data comprising data associated with one or more heart sounds.

In an Example 33, the system of Example 32, further comprising an electrocardiogram (ECG) module configured to provide ECG data, wherein the processor is configured to receive, from the ECG module, the ECG data, and wherein the computer-executable instructions are configured to cause the processor to generate the heart sound data based on the ECG data.

In an Example 34, the system of Example 33, wherein the ECG module is: a component of the mobile device; or a component of an additional device, the additional device comprising at least one of an additional mobile device, a mobile device accessory, an implantable medical device (IMD), and an external medical device (EMD).

In an Example 35, the system of Example 34, wherein the computer-executable instructions are further configured to cause the processor to identify, based on the ECG data, an occurrence of a trigger event, wherein the processor is configured to obtain the acceleration data in response to identifying the occurrence of the trigger event.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

Figure 2:
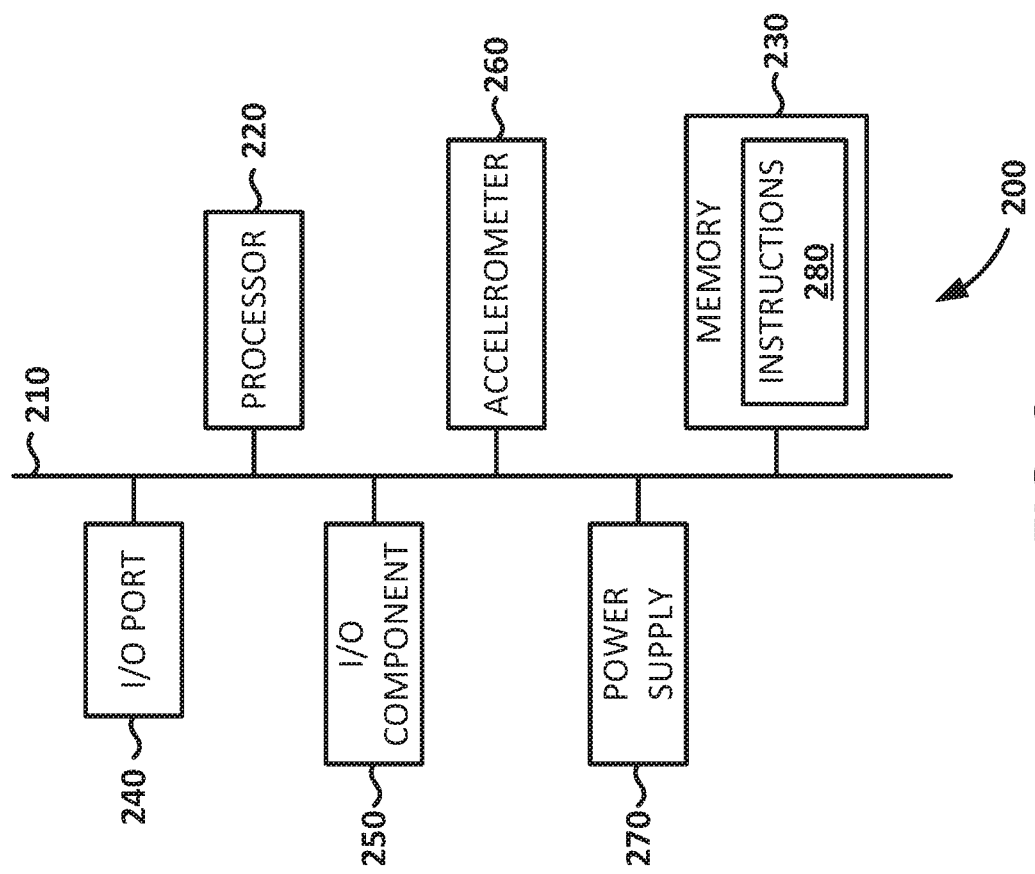
FIG. 2 is a block diagram depicting an illustrative computing device, in accordance with embodiments of the subject matter disclosed herein.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to measurements (e.g., dimensions, characteristics, attributes, components, etc.), and ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information.

DETAILED DESCRIPTION

A "heart sound," as the term is used herein, includes audible and inaudible mechanical vibrations caused by cardiac activity that can be sensed with an accelerometer. Accordingly, when a mechanical sensor such as an accelerometer is used to sense the heart sounds, the scope of energy included in the sensed "acoustic signal" extends to energies associated with such mechanical vibrations. Unless noted otherwise, S1 refers to the first heart sound, S2 refers to the second heart sound, S3 refers to the third heart sound, and S4 refers to the fourth heart sounds, each as a heart sound type, or as one or more occurrences of the corresponding type heart sounds, depending on the context. A "heart beat" includes a cardiac cycle. An "S3 beat" includes a cardiac cycle during which S3 is detected. An "S3 index," also referred to as an "S3 ratio," includes a ratio of the number of the S3 beats to the number of the total heart hearts, both detected during the same time period.

S1 is known to be indicative of, among other things, mitral valve closure, tricuspid valve closure, and aortic valve opening. S2 is known to be indicative of, among other things, aortic valve closure and pulmonary valve closure. S3 is known to be a ventricular diastolic filling sound often indicative of certain pathological conditions including heart failure. S4 is known to be a ventricular diastolic filling sound resulted from atrial contraction and is usually indicative of pathological conditions. Data associated with any number of different heart sounds may be used to diagnose, predict, characterize, control treatment of, and/or otherwise analyze any number of different aspects of conditions, illnesses, states of being, and/or the like.

Figure 1:
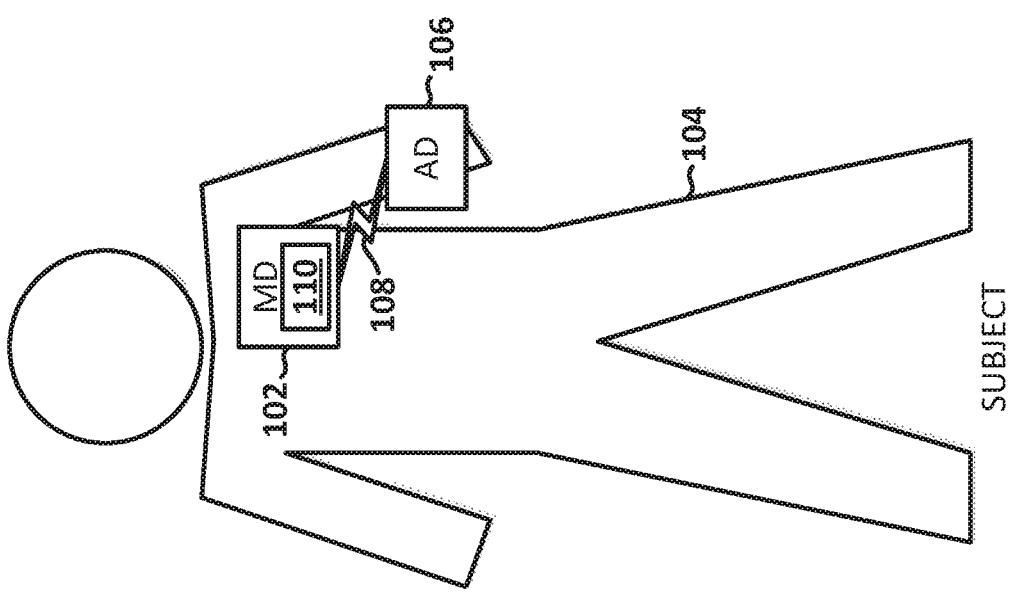
FIG. 1 is a schematic diagram of an illustrative physiological monitoring system, in accordance with embodiments of the subject matter disclosed herein.

FIG. 1 shows an illustrative monitoring system 100, in accordance with embodiments of the disclosure. As shown in FIG. 1, the monitoring system 100 includes a mobile device (MD) 102 configured to be positioned adjacent the body of a subject 104, and an additional device (AD) 106, which is communicatively coupled to the MD 102 via a communication link 108. The MD 102 may be any type of mobile device having computing capabilities such as, for example, a smartphone, a tablet, a notebook, or other portable computing device. In the illustrated embodiments, the monitoring system 100 is operatively coupled to the subject 104, and the MD 102 and the AD 106 are configured to communicate with one another over the communication link 108. The subject 104 may be a human, a dog, a pig, and/or any other animal having physiological parameters that can be recorded. For example, in embodiments, the subject 104 may be a human patient.

In embodiments, the communication link 108 may be, or include, a wired link (e.g., a link accomplished via a physical connection) and/or a wireless communication link such as, for example, a short-range radio link, such as Bluetooth, IEEE 802.11, near-field communication (NFC), WiFi, a proprietary wireless protocol, and/or the like. The term "communication link" may refer to an ability to communicate some type of information in at least one direction between at least two devices, and should not be understood to be limited to a direct, persistent, or otherwise limited communication channel. That is, according to embodiments, the communication link 108 may be a persistent communication link, an intermittent communication link, an ad-hoc communication link, and/or the like. The communication link 108 may refer to direct communications between the MD 102 and the AD 106, and/or indirect communications that travel between the MD 102 and the AD 106 via at least one other device (e.g., a repeater, router, hub, and/or the like). The communication link 108 may facilitate uni-directional and/or bi-directional communication between the MD 102 and the AD 106. Data and/or control signals may be transmitted between the MD 102 and the AD 106 to coordinate the functions of the MD 102 and/or the AD 106. In embodiments, subject data may be downloaded from one or more of the MD 102 and the AD 106 periodically or on command. The clinician and/or the subject may communicate with the MD 102 and/or the AD 106, for example, to acquire subject data or to initiate, terminate and/or modify recording and/or therapy.

In embodiments, the MD 102 and/or the AD 106 may provide one or more of the following functions with respect to a subject: sensing, data analysis, and therapy. For example, in embodiments, the MD 102 and/or the AD 106 may be used to measure any number of a variety of physiological, device, subjective, and/or environmental parameters associated with the subject 104, using electrical, mechanical, and/or chemical means. The MD 102 and/or the AD 106 may be configured to automatically gather data, gather data upon request (e.g., input provided by the subject, a clinician, another device, and/or the like), and/or any number of various combinations and/or modifications thereof. The MD 102 and/or the AD 106 may be configured to store data related to the physiological, device, environmental, and/or subjective parameters and/or transmit the data to any number of other devices in the system 100. In embodiments, the MD 102 and/or the AD 106 may be configured to analyze data and/or act upon the analyzed data. For example, the MD 102 and/or the AD 106 may be configured to modify therapy, perform additional monitoring, and/or provide alarm indications based on the analysis of the data.

In addition, the MD 102 and/or AD 106 may be configured to detect a variety of physiological signals that may be used in connection with various diagnostic, therapeutic and/or monitoring implementations. For example, the MD 102 and/or AD 106 may include sensors or circuitry for detecting respiratory system signals, cardiac system signals, heart sounds. and/or signals related to patient activity. Sensors and associated circuitry may be incorporated in connection with the MD 102 and/or AD 106 for detecting one or more body movement or body posture and/or position related signals. For example, accelerometers and/or GPS devices may be employed to detect patient activity, patient location, body orientation, and/or torso position. Derived parameters may also be monitored using the MD 102 and/or AD 106.

According to embodiments, for example, the MD 102 may include an accelerometer 110 configured to generate an acceleration signal and/or acceleration data, which may include the acceleration signal, information derived from the acceleration signal, and/or the like. In embodiments, the acceleration data includes acceleration measurements associated with movement of the MD 102. In embodiments, the accelerometer may be, or include, any accelerometer known in the art of mobile devices and configured to generate measurements associated with its motion. An "accelerometer," as used herein, may be, or include, any type of accelerometer, gyroscope, inertial measurement unit (IMU), and/or any other type of sensor or combination of sensors configured to measure changes in acceleration, angular velocity, and/or the like.

For example, most smartphones currently include accelerometers configured to generate acceleration data associated with three-dimensional movement of the smartphone (which, in embodiments, may be the MD 102). The inventors have discovered that conventional smartphone accelerometers may be used for detecting heart sounds when the smartphone is positioned in contact with a subject's body in a target region. According to embodiments, a target region is a region in which heart sound signals may be obtained using an accelerometer. That is, for example, when a subject is lying on his or her back, a target region may include the subject's torso or a portion thereof (e.g., the chest); whereas, when a subject is lying on his or her stomach, the target region may include the subject's back. A target location may include any location within a target region and/or a specified location within a target location. According to various embodiments, the target region of a subject may be identified by analyzing acceleration data obtained from the accelerometer to determine, for a given location, whether heart sounds are able to be detected using the accelerometer.

According to embodiments, the MD 102 may be configured to use the accelerometer 110 to detect heart sounds associated with operation of the subject's heart, respiratory parameters associated with the subject's respiration, and/or the like. That is, the MD 102 may be configured to use the accelerometer 110 to generate heart sound data, respiration data, and/or other physiological data. Heart sound data includes information associated with heart sounds such as, for example, identifications of heart sounds, a heart sound signal extracted from an acceleration signal, classifications of heart sounds, statistics or other derived information associated with heart sounds, physiological parameters determined based on heart sounds, and/or the like. Similarly, respiration data includes information associated with respiration such as, for example, identifications of respiratory events and/or stages, a respiration signal extracted from an acceleration (or heart sound) signal, classifications of respiratory events, statistics or other derived information associated with respiration, physiological parameters determined based on respiration information, and/or the like.

In embodiments, the MD 102 and/or the AD 106 may be configured to provide therapy. For example, the MD 102 may be configured to communicate with implanted stimulation devices, infusion devices, and/or the like, to facilitate delivery of therapy. The AD 106 may be, include, or be included in a medical device (external and/or implanted) that may be configured to deliver therapy. Therapy may be provided automatically and/or upon request (e.g., an input by the subject 104, a clinician, another device or process, and/or the like). The MD 102 and/or the AD 106 may be programmable in that various characteristics of their sensing, therapy (e.g., duration and interval), and/or communication may be altered by communication between the devices 102 and 106 and/or other components of the system 100.

According to embodiments, the AD 106 may include any type of medical device, any number of different components of an implantable or external medical system, a mobile device, a mobile device accessory, and/or the like. In embodiments, the AD 106 may include a mobile device accessory such as, for example, a device having an electrocardiogram (ECG) module. An ECG module may include any hardware, software, and/or firmware configured to generate ECG data (e.g., ECG measurements, estimated ECG measurements, information about ECG measurements, information derived from ECG measurements, etc.). The AD 106 may include, for example, an ECG sensor assembly such as, for example, the Kardia Mobile device available from AliveCor, of Mountain View, Calif., USA, which works in conjunction with an app that may be considered to be part of the ECG module. In embodiments, the AD 106 may include, for example, a smart watch such as, for example, a Fitbit, available from Fitbit, Inc., of San Francisco, Calif., USA. In this manner, the ECG module may include components of an AD 106 as well as an MD 102.

In embodiments, the AD 106 may include a medical device. That is, for example, the AD 106 may include a control device, a monitoring device, a pacemaker, an implantable cardioverter defibrillator (ICD), a cardiac resynchronization therapy (CRT) device and/or the like, and may be an implantable medical device known in the art or later developed, for providing therapy and/or diagnostic data about the subject 104 and/or the MD 102. In various embodiments, the AD 106 may include both defibrillation and pacing/CRT capabilities (e.g., a CRT-D device). In embodiments, the AD 106 may be implanted subcutaneously within an implantation location or pocket in the patient's chest or abdomen and may be configured to monitor (e.g., sense and/or record) physiological parameters associated with the patient's heart. In embodiments, the AD 106 may be an implantable cardiac monitor (ICM) (e.g., an implantable diagnostic monitor (IDM), an implantable loop recorder (ILR), etc.) configured to record physiological parameters such as, for example, one or more cardiac electrical signals, heart sounds, heart rate, blood pressure measurements, oxygen saturations, and/or the like.

In various embodiments, the AD 106 may be a device that is configured to be portable with the subject 104, e.g., by being integrated into a vest, belt, harness, sticker; placed into a pocket, a purse, or a backpack; carried in the subject's hand; and/or the like, or otherwise operatively (and/or physically) coupled to the subject 104. The AD 106 may be configured to monitor (e.g., sense and/or record) physiological parameters associated with the subject 104 and/or provide therapy to the subject 104. For example, the AD 106 may be, or include, a wearable cardiac defibrillator (WCD) such as a vest that includes one or more defibrillation electrodes. In embodiments, the AD 106 may include any number of different therapy components such as, for example, a defibrillation component, a drug delivery component, a neurostimulation component, a neuromodulation component, a temperature regulation component, and/or the like. In embodiments, the AD 106 may include limited functionality, e.g., defibrillation shock delivery and communication capabilities, with arrhythmia detection, classification and/or therapy command/control being performed by a separate device.

In embodiments, the AD 106 may include sensing components such as, for example, one or more surface electrodes configured to obtain an electrocardiogram (ECG), one or more accelerometers configured to detect motion associated with the patient 104, one or more respiratory sensors configured to obtain respiration information, one or more environmental sensors configured to obtain information about the external environment (e.g., temperature, air quality, humidity, carbon monoxide level, oxygen level, barometric pressure, light intensity, sound, and/or the like) surrounding the patient 104, and/or the like. In embodiments, the AD 106 may be configured to measure parameters relating to the human body, such as temperature (e.g., a thermometer), blood pressure (e.g., a sphygmomanometer), blood characteristics (e.g., glucose levels), body weight, physical strength, mental acuity, diet, heart characteristics, relative geographic position (e.g., a Global Positioning System (GPS)), and/or the like.

The illustrative cardiac monitoring system 100 shown in FIG. 1 is not intended to suggest any limitation as to the scope of use or functionality of embodiments of the present disclosure. The illustrative cardiac monitoring system 100 should not be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the subject matter disclosed herein.

Various components depicted in FIG. 1 may operate together to form the monitoring system 100, which may be, for example, a computerized patient management and monitoring system. In embodiments, the system 100 may be designed to assist in monitoring the subject's condition, managing the subject's therapy, and/or the like. An illustrative patient management and monitoring system is the LATITUDE® patient management system from Boston Scientific Corporation, Natick Mass. Illustrative aspects of a patient management and monitoring system are described in ADVANCED PATIENT MANAGEMENT SYSTEM INCLUDING INTERROGATOR/TRANSCEIVER UNIT, U.S. Pat. No. 6,978,182 to Mazar et al., the entirety of which is hereby incorporated by reference herein.

Any number of components of the system 100 may be implemented using one or more computing devices. That is, for example, MD 102 and/or AD 106 may be implemented on one or more computing devices. FIG. 2 is a block diagram depicting an illustrative computing device 200, in accordance with embodiments of the disclosure. The computing device 200 may include any type of computing device suitable for implementing aspects of embodiments of the disclosed subject matter. Examples of computing devices include specialized computing devices or general-purpose computing devices such "workstations," "servers," "laptops," "desktops," "tablet computers," "hand-held devices," "smartphones," "general-purpose graphics processing units (GPGPUs)," and the like, all of which are contemplated within the scope of FIGS. 1 and 2, with reference to various components of the system 100 and/or computing device 200.

In embodiments, the computing device 200 includes a bus 210 that, directly and/or indirectly, couples the following devices: a processor 220, a memory 230, an input/output (I/O) port 240, an I/O component 250, an accelerometer 260 (e.g., the accelerometer 110 depicted in FIG. 1), and a power supply 270. Any number of additional components, different components, and/or combinations of components may also be included in the computing device 200. The I/O component 250 may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like.

The bus 210 represents what may be one or more busses (such as, for example, an address bus, data bus, or combination thereof). Similarly, in embodiments, the computing device 200 may include a number of processors 220, a number of memory components 230, a number of I/O ports 240, a number of I/O components 250, a number of accelerometers 260, and/or a number of power supplies 270. Additionally any number of these components, or combinations thereof, may be distributed and/or duplicated across a number of computing devices.

In embodiments, the memory 230 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory 230 stores computer-executable instructions 280 for causing the processor 220 to implement aspects of embodiments of system components discussed herein and/or to perform aspects of embodiments of methods and procedures discussed herein.

The computer-executable instructions 280 may include, for example, computer code, machine-useable instructions, and the like such as, for example, program components capable of being executed by one or more processors 220 associated with the computing device 200. Program components may be programmed using any number of different programming environments, including various languages, development kits, frameworks, and/or the like. Some or all of the functionality contemplated herein may also, or alternatively, be implemented in hardware and/or firmware.

The illustrative computing device 200 shown in FIG. 2 is not intended to suggest any limitation as to the scope of use or functionality of embodiments of the present disclosure. The illustrative computing device 200 also should not be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are considered to be within the ambit of the present disclosure.

Figure 3:
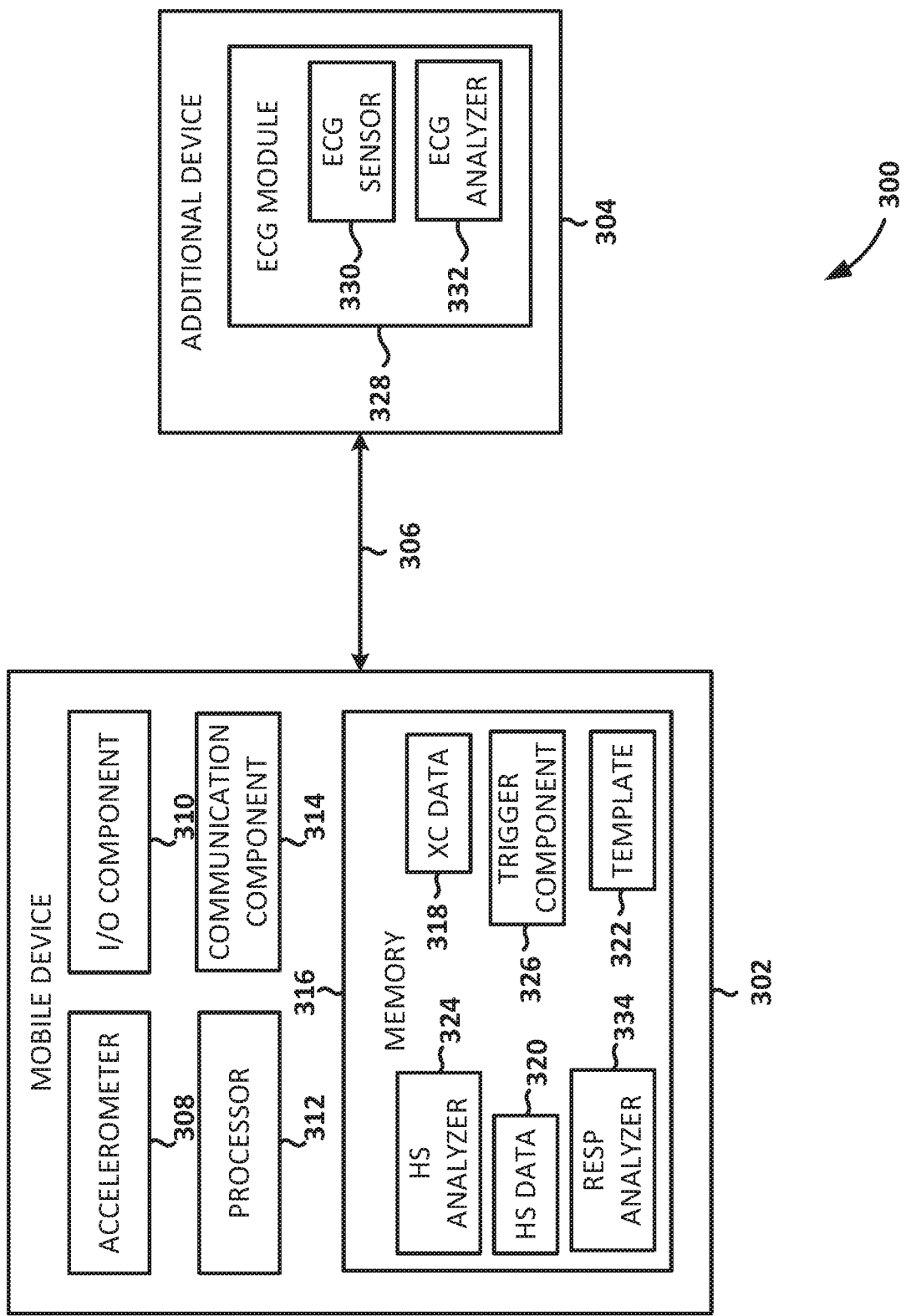
FIG. 3 is a block diagram depicting an illustrative operating environment, in accordance with embodiments of the subject matter disclosed herein.

FIG. 3 is a block diagram depicting an illustrative operating environment 300, in accordance with embodiments of the subject matter disclosed herein. According to embodiments, the operating environment 300 may be, be similar to, include, be included in, or correspond to the system 100 depicted in FIG. 1. As shown in FIG. 3, the illustrative operating environment 300 includes a mobile device 302 configured to communicate with an additional device 304 via a communication link 306. In embodiments, the operating environment 300 may include the mobile device 302 without including an additional device 304. According to embodiments, the mobile device 200 may be, be similar to, include, or be included in the mobile device 102 depicted in FIG. 1; and, similarly, the additional device 304 may be, be similar to, include, or be included in the additional device (AD) 106 depicted in FIG. 1.

According to embodiments, the mobile device 302 may include any type of portable computing device such as, for example, a laptop, a smartphone, a tablet, a notebook, and/or the like. As shown, the mobile device 302 includes an accelerometer 308 (e.g., the accelerometer 110 depicted in FIG. 1 and/or the accelerometer 260 depicted in FIG. 2), an input/output (I/O) component 310 (e.g., the I/O component 250 depicted in FIG. 2), a processor 312 (e.g., the processor 220 depicted in FIG. 2), a communication component 314, and a memory 316 (e.g., the memory 230 depicted in FIG. 3). The processor 312 may execute instructions and perform desired tasks as specified by computer-executable instructions (e.g., the instructions 280 depicted in FIG. 2) stored in the memory 316. The processor 312 may also be configured to store information in the memory 316 and/or access information from the memory 316. For example, in embodiments, the processor 312 may be configured to store and/or access acceleration (XC) data 318, heart sound (HS) data 320, HS templates 322, and/or the like.

The memory 316 may include volatile and/or non-volatile memory, and may store instructions that, when executed by the processor 312 cause methods and processes to be performed by the mobile device 302. For example, in embodiments, the processor 312 may process instructions and/or data stored in the memory 316 to facilitate detection and/or analysis of heart sounds. In embodiments, the processor 312 may receive acceleration data 318 from the accelerometer 308 and may instantiate (e.g., from the memory 316) a heart sound (HS) analyzer 324 to generate, based on the acceleration data 318, heart sound data 320. The acceleration data may include, for example, an acceleration signal (e.g., a number of acceleration measurements); and the heart sound data may include information associated with heart sounds such as, for example, identifications of heart sounds, classifications of heart sounds, statistics associated with heart sounds, physiological parameters derived from heart sound data, and/or the like. In embodiments, the processor 312 may be configured to cause an I/O component 310 to present a representation of the heart sound data 320 and/or other information (e.g., physiological parameters, environmental parameters, device parameters, etc.), cause the communications component 314 to communicate heart sound data and/or other information (e.g., physiological parameters, environmental parameters, device parameters, etc.) to another device (e.g., the additional device 304, and/or a device not shown in FIG. 3), and/or the like.

According to embodiments, the heart sound data 320 may be generated by the HS analyzer 324. In embodiments, the HS analyzer 324 may be configured to generate heart sound data 320 by performing any number of different processes such as, for example, filtering, interpolating, and/or the like. In embodiments, the HS analyzer 324 may be configured to standardize the acceleration data before further processing it. Many conventional accelerometers are configured to take measurements in response to a demand for acceleration data and, often, those measurements are taken using sample rates that are dynamically determined based on the movement of the mobile device, the reason for the data, and/or the like. Accordingly, acceleration data often is not generated using a fixed sampling rate. Thus, the HS analyzer 324 may be configured to standardize the acceleration data—that is, to perform a process on the acceleration data that changes it into standardized acceleration data, which is acceleration data that has been modified to estimate what the acceleration data would be if it had been generated using a fixed sampling rate. In embodiments, the HS analyzer 324 may be configured to perform a data interpolation process on the acceleration data to generate standardized acceleration data. The interpolation may be configured to generate standardized acceleration data based on templates, internal characteristics of the acceleration data, known information, and/or the like.

According to embodiments, the HS analyzer 324 may be configured to generate heart sound data, based on the acceleration data, by performing a noise reduction process on the standardized acceleration data. In embodiments, performing the noise reduction process on the standardized acceleration data may include performing at least one of: spectral filtering (e.g., by attenuating specified frequencies, frequency bands, etc.), bandpass filtering (e.g., by attenuating frequency bands above and/or below specified thresholds), high pass filtering (e.g., by attenuating frequencies below a specified threshold to remove DC offsets), and/or the like. Attenuating components of a signal, as described herein, may include removing, suppressing, transforming, or otherwise attenuating the component of the signal as is understood by those having skill in the relevant arts. In this manner, noise reduction may be performed by rejecting signal values that are not likely to include heart sound information.

In embodiments, for example, a frequency band and/or threshold corresponding to heart sounds of a subject may be determined using information from the mobile device 302, the additional device 304, an implanted device, and/or the like, and used to filter an acceleration signal (and/or standardized acceleration signal) to attenuate acceleration data that is not associated with heart sounds. It has been discovered, for example, that components of an acceleration signal having a frequency above approximately 200 Hertz are generally not associated with heart sounds. Thus, in embodiments, the HS analyzer 324 may be configured to attenuate the component of the accelerometer signal not associated with heart sounds such as, for example, by attenuating accelerometer data having frequencies above approximately 200 Hertz. In some embodiments, this may be the only filtering process performed on the standardized acceleration signal, while, in other embodiments, other filtering process may be performed in addition to, or in lieu of, this frequency filtering. For example, in embodiments, the accelerometer signal may be band-pass filtered having a band-pass of between approximately 0 Hertz and approximately 200 Hertz (e.g., approximately 0-approximately 100 Hertz, approximately 20-approximately 70 Hertz, etc.) to isolate portions of the signal unrelated to the heart sounds.

In embodiments, the HS analyzer 324 may be configured to a pattern recognition process on the standardized acceleration data. The pattern recognition process may be performed, for example, by identifying a heart sound window; and identifying, within the heart sound window, the one or more heart sounds. The heart sound window, which refers to a temporal portion of the standardized acceleration signal that is determined to be likely to include heart sound signals, may be identified using any number of different techniques such as, for example, peak detection algorithms, template-matching algorithms, and/or the like. It is known, for example, that a series of heart sounds occur every time a subject's heart beats. Conventionally, identification of the R-wave in a subject's ECG is used to determine a heart sound window. In embodiments in which an ECG signal is available, this may be done.

In embodiments in which an ECG signal is not available (or embodiments in which the ECG signal is not used, or is not the only signal used), a heart sound detection algorithm may be used to detect one or more heart sounds by identifying a specified feature of the one or more heart sounds. For example, a peak detection algorithm may be used to detect peak amplitudes associated with the S1 and/or S2 heart sounds. Upon detecting the one or more heart sounds, the HS analyzer 324 may be configured to select a heart sound window (e.g., a selection of the standardized acceleration signal within which one or more additional heart sounds are expected to be found (e.g., an S3 heart sound) based on the detected heart sound(s).

In embodiments, the heart sound window may be identified based on analysis of electrocardiogram (ECG) data, which may be obtained, for example, from an ECG module 328, which may be, in embodiments, instantiated on the mobile device 302 and/or the additional device 304, although the ECG module 328 is shown as being instantiated by the additional device 304 in FIG. 3. According to embodiments, the ECG module 328 may include one or more ECG sensors 330 configured to sense cardiac electrical signals, and an ECG analyzer 332 configured to analyze the electrical signals to generate ECG data. The HS analyzer 324 may be configured to obtain ECG data from the ECG module 328 and to use the ECG data in determining the heart sound window. In embodiments, for example, the heart sound window may be determined based on identification of a temporal location of an R-wave.

In embodiments, one or more heart sound templates 322 may be used, in a template matching process, to identify heart sounds within the heart sound window. In embodiments, heart sound templates 322 may be generated by the HS analyzer 324 based on any number of portions of an acceleration signal (and/or standardized acceleration signal). In embodiments, heart sound templates 322 may be stored in the memory 316 and may be obtained, e.g., from a database of heart sound templates, from the additional device 304, and/or the like. That is, for example, in embodiments, the additional device 304 may be configured to generate one or more heart sound templates 322. Heart sound templates 322 may be configured to facilitate identification of heart sounds based on any number of different characteristics such as, for example, spectral content, amplitudes, morphology, and/or the like.

In embodiments, for example, embodiments may include an HS analyzer 324 configured to extract S3 heart sounds from an acceleration signal. The HS analyzer 324 may be configured to use a peak detection algorithm to identify S1 and S2 heart sounds and, using multiple occurrences of the S1 and S2 heart sounds across periodic samples, the HS analyzer 324 may be configured to determine a detection window for detecting the S3 heart sound. In embodiments, the HS analyzer 324 may be configured to identify the S3 heart sounds by sliding the S3 detection window to different temporal locations and analyzing the acceleration data associated with the portions of the acceleration data within the window at various points. The HS analyzer 324 may be configured to perform ensemble averaging across a number of heart beats to increase the signal-to-noise ratio (SNR) of the extracted S3 heart sound data.

According to embodiments, acceleration signals 318 may be used to generate respiration data, activity data, and/or other data associated with a subject. For example, the mobile device may include a respiration (RESP) analyzer 334 configured to analyze an acceleration signal 318 and/or standardized acceleration signal 318 to generate respiration data. Respiration parameters may be detected, for example, based on deflections of the acceleration signal 318, spectral analysis of the acceleration signal 318, and/or the like. In embodiments, the mobile device may be configured to develop, based on acceleration data, a respiration profile associated with a subject, and may be configured to use the respiration profile to facilitate identification of heart sounds in additional respiration data. According to embodiments, acceleration signals 318 may be used to detect and/or characterize subject activity, which may facilitate sampling configuration and/or the like. For example, in embodiments, the mobile device 302 may be configured to detect large motions (e.g., associated with the body of the subject) and, in response to detecting those motions, discontinue obtaining acceleration data for use in detecting heart sounds, or otherwise account for the motion.

The HS analyzer 324 and/or RESP analyzer 334 may be configured to use various algorithms and mathematical modeling such as, for example, trend and statistical analysis, data mining, pattern recognition, cluster analysis, neural networks and/or fuzzy logic. The HS analyzer 324 and/or RESP analyzer 334 may perform deterministic and probabilistic calculations. Deterministic calculations include algorithms for which a clear correlation is known between the data analyzed and a given outcome.

As shown in FIG. 3, the mobile device also may include a trigger component 326 configured to identify an occurrence of a trigger event. A trigger event is any designated event that, upon identification of its occurrence, results in some action. That is, for example, in embodiments, the mobile device may be configured (e.g., using the trigger component 326) to identify the occurrence of a trigger event and cause the processor, in response to identifying the occurrence of a trigger event, to obtain the acceleration data. In embodiments, the mobile device may be configured to identify the occurrence of a trigger event by determining that the mobile device is located at a target location on the subject; determining that the mobile device is positioned in a target position with respect to the subject; receiving an indication of a user input; determining that a parameter (e.g., a physiological parameter, an environmental parameter, and/or a device parameter) satisfies one or more trigger criteria; and/or the like.

According to embodiments, the trigger event may include an occurrence of a specified physiological parameter. For example, in embodiments, the HS analyzer 324 may be configured to receive electrocardiogram (ECG) data from an ECG module 328; and obtain an acceleration signal, generate heart sound data, and/or otherwise perform some designated task in response to identifying the occurrence of a specified characteristic (e.g., an R-wave) of the ECG data. Similarly, in embodiments, the HS analyzer 324 may be configured to receive respiratory data from a RESP analyzer 334; and obtain an acceleration signal, generate heart sound data, and/or otherwise perform some designated task in response to identifying the occurrence of a specified characteristic (e.g., a stage of a respiration cycle) of the respiration data.

According to embodiments, the trigger component 326 may be configured to implement any number of different adjudication algorithms to detect a trigger event. The trigger component 326 may detect a trigger event based on information received from any number of other components, devices, and/or the like. For example, the trigger component 326 may obtain physiological parameter information from the additional device 304 and may use that physiological parameter information to detect a trigger event. In an example, the trigger component 326 may be configured to detect changes in one or more physiological parameter, based on trigger criteria. In other examples, the trigger component 326 may be configured to determine a trigger event at a predetermined time, during a predetermined time interval, and/or the like. Trigger events may be user defined, system defined, statically defined, dynamically defined, and/or the like. The trigger component 326 may reference trigger criteria stored in memory 316 to determine whether a trigger event has occurred. The trigger criteria may be established by a clinician, a patient, an algorithm, and/or the like.

For example, in embodiments, the trigger component 326 may reference a first set of trigger criteria for determining whether a first trigger event has occurred, a second set of trigger criteria for determining whether a second trigger event has occurred, and/or the like. The first trigger event may be, for example, an identification of activity of the subject. Because different subjects may have different average heart rates and heart rate characteristics, the trigger criteria for detecting activity as a trigger event may be different for a first subject than it is for a second subject. Any number of other types of events may be used as trigger events such as, for example, specified times of day, specified states of the mobile device 302 or one or more components thereof, an alarm state of the mobile device (e.g., provided using an alarm feature), a geographic location of the mobile device (e.g., determined using a GPS or similar feature), detection of specified WiFi signals, receipt of a signal from an additional device 304, and/or the like.

In embodiments, to detect a trigger event based on a first trigger event, the trigger component 326 may also be configured to obtain information associated with a second trigger event. A set of trigger criteria also may be dynamically adapted over time, using a machine-learning process. That is, for example, as a subject ages, adopts changes to daily routines (e.g., diet, exercise, sleep habits, etc.), and/or the like, the trigger component 326 may dynamically adapt trigger criteria so that, for example, a smaller level of activity may be detected as a trigger event when the patient is older than when the patient was younger. Additionally, machine-learning techniques may be employed to adapt trigger criteria to more rapidly-changing scenarios such as, for example, the impact of adjusting to a new medication, the impact of a temporary adjustment in sleep schedule, the impact of the air quality in a particular location (e.g., outside vs. inside, downtown vs. at home, one city vs. another, etc.), the impact of an allergic reaction to an environmental stimulus, the impact of a psychological response to an increase or decrease in an amount of sunlight over the course of one or more days, the impact of a rapid change in barometric pressure, and/or the like. According to embodiments, adapting a set of trigger criteria may include adjusting one or more thresholds, adjusting one or more value ranges, adding or subtracting types of information to be considered (e.g., requiring additional, or fewer, inputs to an adjudication algorithm), adjusting weight applied to one or more inputs, adjusting error terms, adjusting boundary conditions, and/or the like.

According to embodiments, the trigger component 326 may be configured to use a location-based algorithm to identify an occurrence of a trigger event by determining that the mobile device 302 is located at a target location (e.g., within a target region) on the subject and/or determine that the mobile device 302 is positioned in a target position with respect to the subject (e.g., lying on the subject's body, in contact with the subject's skin, and/or the like). In embodiments, the trigger component 326 may be configured to use one or more machine-learning techniques to learn to determine when the mobile device 302 is located at a target location and/or positioned in a target position by analyzing data such as, for example, acceleration data, GPS data, calendar data, and/or the like. For example, in embodiments, for example, entropy of an auto-correlation of an acceleration signal with itself may be used determine whether the mobile device 302 is located in a target location, since a heart sound signal is a repetitive signal, which will result in a change in the entropy. Any number of different types of templates, algorithms, and/or the like may be used to identify an occurrence of a trigger event associated with location and/or position of the mobile device 302.

For example, in embodiments, the trigger component 326 may be configured to receive an acceleration signal 318 from the accelerometer 308, determine one or more characteristics of the acceleration signal 318, and determine whether the one or more characteristics of the acceleration signal 318 satisfy one or more criteria. For example, the processing unit may determine that the acceleration signal 318 likely includes heart sounds if the one or more characteristics of the acceleration signal 318 satisfy the one or more criteria. In this manner, the trigger component 326 may be able to differentiate between different types of acceleration signals. In embodiments, the trigger component 326 may analyze an acceleration signal (and/or other signal from another component of the mobile device 302, additional device 304, and/or the like) to determine whether a characteristic of the signal satisfies one or more criteria such as, for example, a designated range, threshold, and/or the like.

Using specified criteria, the trigger component 326 can be configured to differentiate between trigger events and other events that may be accidental, or otherwise natural, occurrences such as, for example, heart beats, vibrations and other measurable changes caused by the patient engaging in activity (e.g., impacts between the patient's feet and the ground), signals caused by sound waves impinging on the surface of the patient's body (e.g., at concerts, in theaters, etc.), and/or the like.

In embodiments, the trigger component 326 may be further configured to cause an I/O component 310 to present an indication that the mobile device is located at a target location and/or positioned in a target position. In embodiments, for example, trigger component 326 may be configured to cause the I/O component to present an instruction to a user (e.g., the subject, an assistant to the subject, a clinician, etc.) to place the mobile device 302 within a specified region on the subject's body. The trigger component 326 may be configured to initiate a location-based trigger algorithm in response to determining that the mobile device has stopped moving (e.g., after a brief period of movement following the presentation of the instruction). If the trigger component 326 determines that the mobile device 302 is not located at a target location and/or positioned in a target position, the trigger component 326 may cause the I/O component 310 to present an indication to the user that the mobile device 302 is not located at a target location and/or positioned in a target position. In response to determining that the mobile device 302 is located at a target location and/or positioned in a target position, the trigger component 326 may be configured to generate an indication of that fact (a representation of which may be presented by the I/O component), and provide that indication to the processor 312 (and/or the HS analyzer 324), in response to which the process of monitoring heart sounds may be initiated.

According to embodiments, the processor 312 may be configured to instantiate (e.g., by executing, from the memory 316; by calling; by initializing; by creating; etc.) the trigger component 326 to detect an occurrence of a trigger event and, in response to detecting the occurrence of the trigger event, cause the mobile device 302 to transition from a first state to a second state. In embodiments, the trigger component 326 causes the mobile device 302 to transition from a first state to a second state by communicating a detection signal to the processer 312, which transitions the mobile device 302 from the first state to the second state. In embodiments, the first and/or second states of the mobile device 302 may correspond to any one or more of the components illustrated in FIG. 3, components not illustrated in FIG. 3, aspects of embodiments of functionalities of one or more of the aforementioned components, and/or the like.

For example, in embodiments, the processor 312 may be configured to cause the accelerometer 308 to transition from a first state, in which the accelerometer 308 is dormant, to a second state, in which the accelerometer 308 is configured to actively sense acceleration. In embodiments, the processor 312 may be configured to instantiate the HS analyzer 324 (e.g., transitioning the mobile device 302 from a first state, in which the HS analyzer 324 is not instantiated, to a second state, in which the HS analyzer 324 is instantiated); cause the HS analyzer 324 to obtain acceleration data from the accelerometer; prompt a user for information; provide an instruction to a user (e.g., to direct the user to place the mobile device 302 in a target region on a subject); begin presenting real-time representations of heart sound data (e.g., representations presented within a specified time period of generating the heart sound data); and/or the like.

As shown in FIG. 3, the mobile device 302 includes a communication component 314 having circuits and one or more transmitters and/or receivers for communicating with the additional device 304. Similarly, a communication component (not shown) of the additional device 304 is configured to communicate, via the communication component 314, with the mobile device 302. For example, the communication component 314 of the mobile device 302 may be configured to communicate one or more physiological parameters to the additional device 304. In embodiments, the communication component 314 may also facilitate communications with other devices such as, for example, to facilitate coordinated operations between the devices. According to various embodiments, the communication component 314 may include one or more transmitters, receivers, transceivers, transducers, and/or the like, and may be configured to facilitate any number of different types of wireless communication such as, for example, radio-frequency (RF) communication, microwave communication, infrared communication, acoustic communication, inductive communication, conductive communication, and/or the like.

Any number of various components of the operating environment 300 depicted in FIG. 3 may be communicatively coupled via the communication link 306. The communication link 306 may provide for communications between and among various components of the operating environment 300, such as the devices 302 and 304. The communication link 306 may be, be similar to, include, or be included in the communication link 108 depicted in FIG. 1, and/or any number of different types of communication networks such as, for example, a bus network, a short messaging service (SMS), a local area network (LAN), a wireless LAN (WLAN), a wide area network (WAN), the Internet, a P2P network, custom-designed communication or messaging protocols, and/or the like. The communication link 306 may include a combination of multiple networks, which may be wired and/or wireless.

The illustrative operating environment shown in FIG. 3 is not intended to suggest any limitation as to the scope of use or functionality of embodiments of the present disclosure. The illustrative operating environment 300 also should not be interpreted as having any dependency or requirement related to any single component or combination of components illustrated therein. Additionally, various components depicted in FIG. 3 may be, in embodiments, integrated with various ones of the other components depicted therein (and/or components not illustrated), all of which are considered to be within the ambit of the present disclosure.

Figure 4:
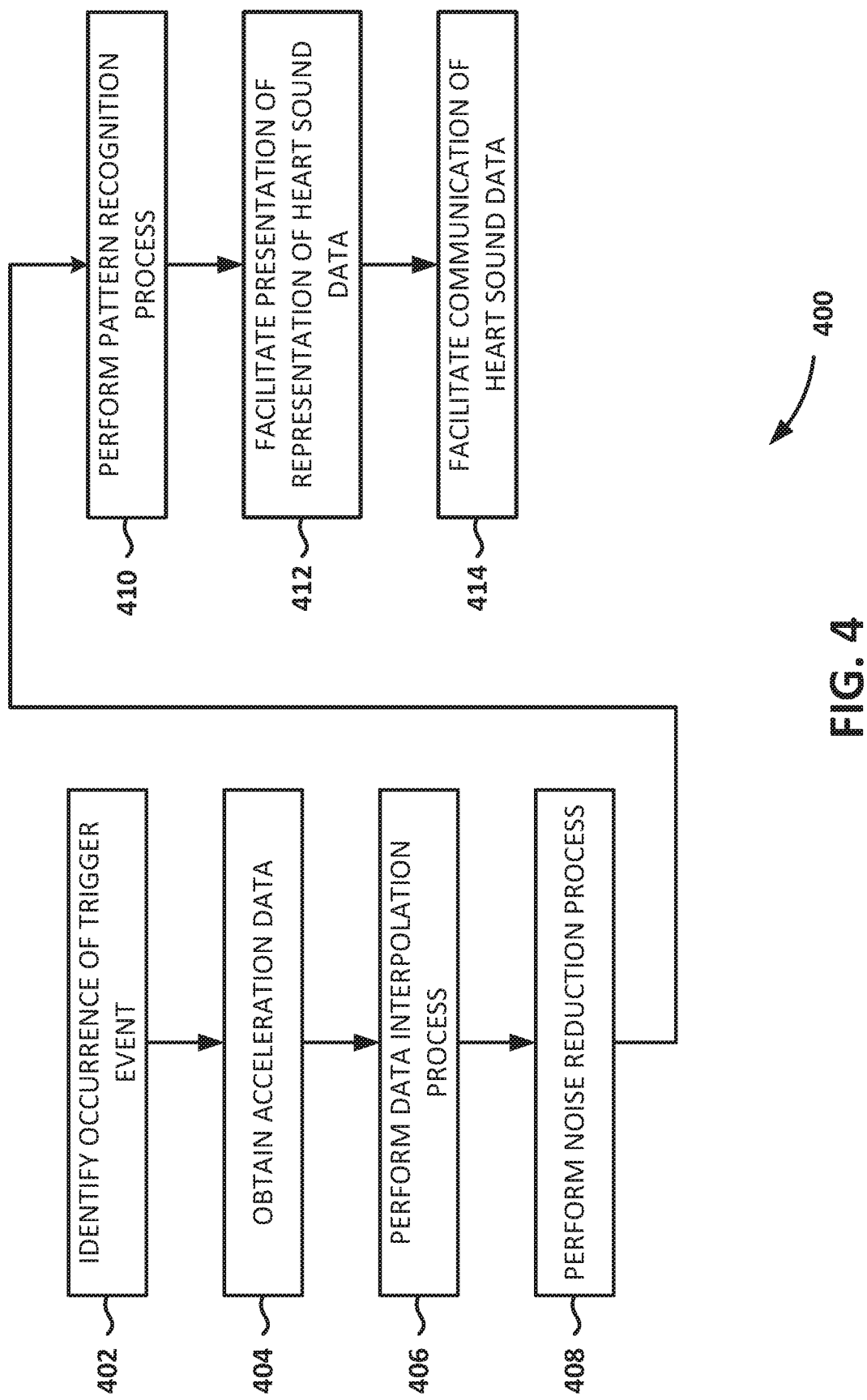
FIG. 4 is a flow diagram depicting an illustrative method of physiological monitoring, in accordance with embodiments of the subject matter disclosed herein.

FIG. 4 is a flow diagram depicting an illustrative method 400 of physiological monitoring (e.g., monitoring heart sounds), in accordance with embodiments of the subject matter disclosed herein. According to embodiments, the method 400 may be performed by any number of different aspects of components of the system 100 depicted in FIG. 1, the computing device 200 depicted in FIG. 2, and/or the operating environment 300 depicted in FIG. 3. For example, in embodiments, the illustrative method 400 may be performed by a mobile device having an accelerometer, a processor, and a memory, as described herein.

Embodiments of the method 400 include identifying an occurrence of a trigger event (block 402) and obtaining, in response to identifying the occurrence of the trigger event, acceleration data from the accelerometer (block 404). According to embodiments, identifying the occurrence of the trigger event may include determining that the mobile device is located at a target location on the subject; determining that the mobile device is positioned in a target position with respect to the subject; receiving an indication of a user input; and/or determining that a parameter (e.g., a physiological parameter, an environmental parameter, and/or a device parameter) satisfies one or more trigger criteria.

As is further shown in FIG. 4, embodiments of the method 400 include performing a data interpolation process on the acceleration data to generate standardized acceleration data (block 406). The method 400 may include performing a noise reduction process on the standardized acceleration data (block 408). In embodiments, performing the noise reduction process on the standardized acceleration data may include performing at least one of spectral filtering, bandpass filtering, and high pass filtering.

As shown in FIG. 4, the method 400 may include performing a pattern recognition process on the standardized acceleration data to identify one or more heart sounds (block 410), thereby generating heart sound data. According to embodiments, performing the pattern recognition process may include identifying a heart sound window; and identifying, within the heart sound window and using a template matching process, the one or more heart sounds. Embodiments of the method may further include facilitating presentation of a representation of the heart sound data (block 412) and/or communicating the heart sound data (block 414). According to embodiments, the method 400 may include any number of other steps, alternative steps, alternative orders of steps, and/or the like. For example, in embodiments, the method 400 may include receiving electrocardiogram (ECG) data and generating the heart sound data based on the ECG data.

Various modifications and additions can be made to the exemplary embodiments discussed without departing from the scope of the presently disclosed subject matter. For example, while the embodiments described above refer to particular features, the scope of this disclosure also includes embodiments having different combinations of features and embodiments that do not include all of the described features. That is, for example, in embodiments, an ECG signal may be used in conjunction with heart sound data to characterize an electro-mechanical delay associated with the subject's heart. Accordingly, the scope of the subject matter disclosed herein is intended to embrace all such alternatives, modifications, and variations as fall within the scope of the claims, together with all equivalents thereof.

We claim:

1. A mobile device having a processor, comprising:
   an accelerometer included in the mobile device and configured to generate acceleration data, the acceleration data comprising a plurality of acceleration measurements taken with a plurality of sampling rates that are dynamically determined based on three-dimensional movement of the mobile device positioned externally adjacent to a body of a subject;
   a memory having embodied thereon computer-executable instructions that are configured to, when executed by the processor, cause the processor to:
      obtain the acceleration data from the accelerometer;
      perform a data interpolation process on the acceleration data to generate standardized acceleration data with a fixed sampling rate; and
      generate, based on the standardized acceleration data, heart sound data, the heart sound data comprising data associated with one or more heart sounds.

2. The mobile device of claim 1, further comprising a display device configured to present a representation of the heart sound data and wherein the mobile device is a mobile phone.

3. The mobile device of claim 1, wherein the computer instructions are configured to cause the processor to generate the heart sound data by:
   performing a noise reduction process on the standardized acceleration data; and
   performing a pattern recognition process on the standardized acceleration data to identify one or more heart sounds.

4. The mobile device of claim 3, wherein performing the noise reduction process on the standardized acceleration data comprises performing at least one of:
   spectral filtering, bandpass filtering, and high pass filtering.

5. The mobile device of claim 3, wherein performing the pattern recognition process comprises:
   identifying a heart sound window; and
   identifying, within the heart sound window, the one or more heart sounds.

6. The mobile device of claim 5, wherein identifying the one or more heart sounds is performed using a template matching process.

7. The mobile device of claim 1, wherein the computer-executable instructions are configured to cause the processor to identify an occurrence of a trigger event, and to cause the processor to obtain the acceleration data in response to identifying the occurrence of the trigger event, wherein the computer-executable instructions are configured to cause the processor to identify the occurrence of the trigger event by causing the processor to:

determine that the mobile device is located at a target location on the subject;
determine that the mobile device is positioned in a target position with respect to the subject;
receive an indication of a user input; and/or
determine that a parameter satisfies one or more trigger criteria, the parameter comprising at least a physiological parameter, an environmental parameter, and a device parameter.

8. The mobile device of claim 1, wherein the computer-executable instructions are further configured to cause the processor to:
receive electrocardiogram (ECG) data from an ECG module; and
generate the heart sound data based on the acceleration data and the ECG data.

9. The mobile device of claim 8, wherein the computer-executable instructions are configured to cause the processor to generate the heart sound data based on the ECG data by using the ECG data to facilitate identifying one or more heart sound windows corresponding to the heart sound data.

10. The mobile device of claim 8, wherein the ECG module is:
a component of the mobile device; or
a component of an additional device, the additional device comprising at least one of an additional mobile device, a mobile device accessory, an implantable medical device (IMD), and an external medical device (EMD).

11. A method of monitoring heart sounds using a mobile device having an accelerometer, the method comprising:
obtaining the acceleration data from the accelerometer included in the mobile device, the acceleration data being taken with a plurality of sampling rates that are dynamically determined based on three-dimensional movement of the mobile device positioned externally adjacent to a body of a subject;
performing a data interpolation process on the acceleration data to generate standardized acceleration data with a fixed sampling rate; and
generating, based on the standardized acceleration data, heart sound data, the heart sound data comprising data associated with one or more heart sounds.

12. The method of claim 11, further comprising presenting, using a display device, a representation of the heart sound data and wherein the mobile device is a mobile phone.

13. The method of claim 11, wherein generating the heart sound data comprises:
performing a noise reduction process on the standardized acceleration data; and
performing a pattern recognition process on the standardized acceleration data to identify one or more heart sounds.

14. The method of claim 11, further comprising identifying an occurrence of a trigger event, wherein the step of obtaining the acceleration data is performed in response to identifying the occurrence of the trigger event.

15. The method of claim 11, wherein identifying the occurrence of the trigger event comprises:
determining that the mobile device is located at a target location on the subject;
determining that the mobile device is positioned in a target position with respect to the subject;
receiving an indication of a user input; and/or
determining that a parameter satisfies one or more trigger criteria, the parameter comprising at least one of a physiological parameter, an environmental parameter, and a device parameter.

16. The method of claim 11, further comprising:
receiving electrocardiogram (ECG) data; and
generating the heart sound data based on the ECG data.

17. A system for monitoring heart sounds, comprising:
a mobile device configured to be positioned externally adjacent to a body of a subject, the mobile device comprising:
an accelerometer included in the mobile device and configured to generate acceleration data, the acceleration data comprising a plurality of acceleration measurements taken with a plurality of sampling rates that are dynamically determined based on three-dimensional movement of the mobile device;
a processor communicatively coupled to the accelerometer; and
a memory having embodied thereon computer-executable instructions that are configured to, when executed by the processor, cause the processor to obtain the acceleration data from the accelerometer, perform a data interpolation process on the acceleration data to generate standardized acceleration data with a fixed sampling rate, and to generate, based on the standardized acceleration data, heart sound data, the heart sound data comprising data associated with one or more heart sounds.

18. The system of claim 17, further comprising an electrocardiogram (ECG) module configured to provide ECG data, wherein the processor is configured to receive, from the ECG module, the ECG data, and wherein the computer-executable instructions are configured to cause the processor to generate the heart sound data based on the ECG data.

19. The system of claim 18, wherein the ECG module is:
a component of the mobile device; or
a component of an additional device, the additional device comprising at least one of an additional mobile device, a mobile device accessory, an implantable medical device (IMD), and an external medical device (EMD).

20. The system of claim 19, wherein the computer-executable instructions are further configured to cause the processor to identify, based on the ECG data, an occurrence of a trigger event, wherein the processor is configured to obtain the acceleration data in response to identifying the occurrence of the trigger event.

* * * * *